United States Patent [19]

Branscombe et al.

[11] 3,942,356
[45] Mar. 9, 1976

[54] ON-LINE CARBON DIOXIDE ANALYZER AND ANALYZING METHOD

[75] Inventors: Richard Alan Branscombe; Arthur Caputi, Jr., both of Modesto, Calif.

[73] Assignee: E. & J. Gallo Winery, Modesto, Calif.

[22] Filed: Sept. 30, 1974

[21] Appl. No.: 510,812

[52] U.S. Cl. .................................. 73/19; 73/61 R
[51] Int. Cl.² .......................................... G01N 7/00
[58] Field of Search ............................ 73/19, 61 R

[56] References Cited
UNITED STATES PATENTS

| | | |
|---|---|---|
| 3,150,516 | 9/1964 | Linnenbom et al. ............... 73/19 |
| 3,438,241 | 4/1969 | McKinley, Jr. .................. 73/19 X |
| 3,673,853 | 7/1972 | Griswold et al. ..................... 73/19 |

Primary Examiner—Herbert Goldstein

[57] ABSTRACT

Apparatus and method for determining the amount of carbon dioxide in continuously supplied liquids containing dissolved carbon dioxide, such as wine or other beverages. A constant-flow sidestream of the liquid is ejected in the presence of a carrier gas which dissolves carbon dioxide into a separating chamber under conditions which yield substantially instantaneous and substantially complete evolution of carbon dioxide from the liquid. The carrier gas and evolved carbon dioxide are conducted from the chamber to a carbon dioxide measuring and recording device, and the separated liquid that is depleted of carbon dioxide is drained from the chamber.

13 Claims, 2 Drawing Figures

U.S. Patent    March 9, 1976    3,942,356
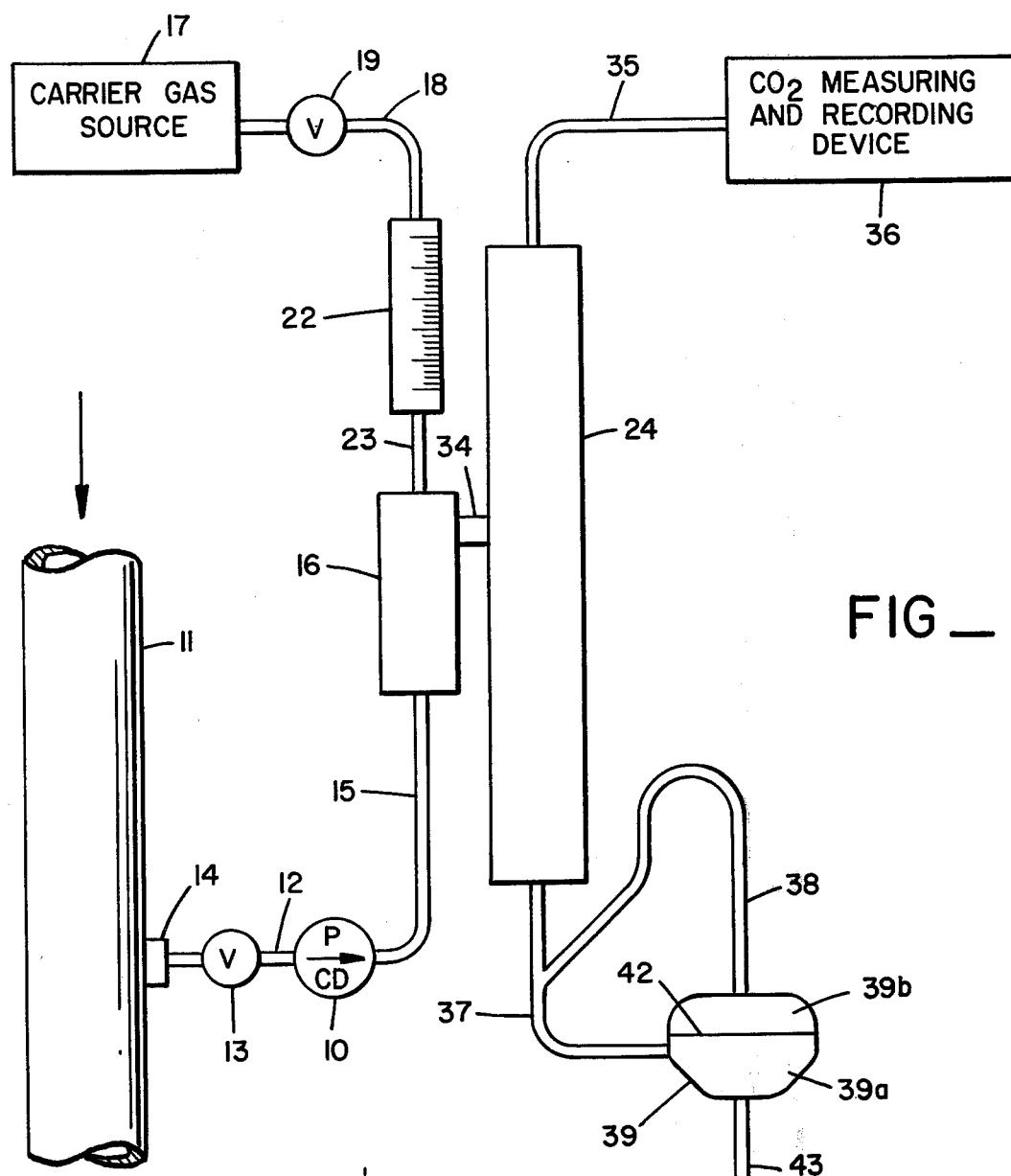
FIG_1
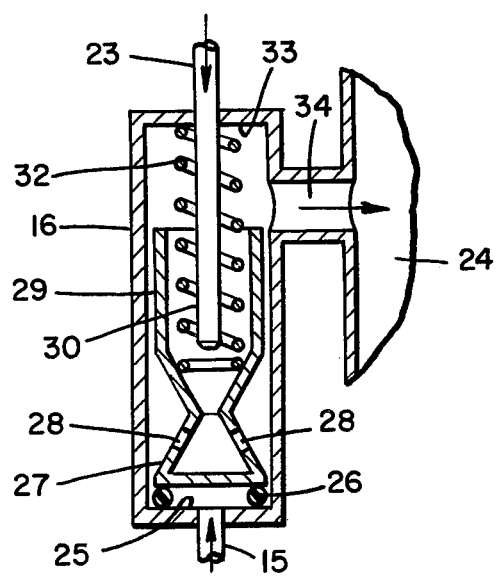
FIG_2

ON-LINE CARBON DIOXIDE ANALYZER AND ANALYZING METHOD

BACKGROUND OF THE INVENTION

This invention relates generally to determination of the level of dissolved carbon dioxide in liquids. More specifically, it pertains to apparatus and a method for continuous analysis of the amount of dissolved $CO_2$ in beverages or other liquids during a bottling process, and is particularly suited for "on-line" application, as for example, in analyzing wine or beer supplied from the line feeding bottle filler apparatus.

It has been recognized that it is exceedingly difficult to obtain consistent and accurate measurements of $CO_2$ in beverages during bottling because of the inherent unpredictability of $CO_2$ when subjected to the conditions of known analyzing techniques. However, accurate determination of $CO_2$ content is of importance for maintenance of product quality and satisfaction of Federal regulations applicable to consumed liquids.

One prior technique employed in analyzing wine, for example, relies upon diffusion of $CO_2$ through a semipermeable membrane tapped into the wine line. The diffused gas is introduced into a nitrogen stream which is then fed at a constant flow rate to an infrared analyzer adapted for determining relative $CO_2$ concentration. The technique suffers the drawback of yielding only a relative rather than a quantitative reading. It is further deficient as providing non-uniform results since variations in alcoholic content, dissolved solids in the wine, temperature, membrane permeability, interruptions in the bottle-filling operation and other factors affect the readings obtained.

Heretofore, the procedures employed in analyzing $CO_2$ in beverages such as wines, as standardized by the Association of Official Analytic Chemists, and set forth in *Official Methods of Analysis* (1970) 11th. Ed., A.O.A.C., have mainly been directed to time-comsuming manual techniques which have provided less than desirably accurate and reproducible results and do not present a continuous reading. These techniques do not satisfy the need for a continuous analyzing method for maintaining a uniform level of $CO_2$ in wines and other beverages bottled at high speeds. Of the best known manual methods, the manometric method (AOAC 11.053–11.057) and volumetric method (AOAC 11.058–11.060) are particularly time-consuming, and the enzymatic method (AOAC 11.061–11.062), while somewhat quicker, is frequently found to be an inconveniently difficult procedure. All these methods require rigorous sample preparation and meticulous manipulations with chemical reagents. Recent proposals for analysis of $CO_2$ in wines have been concerned with modifications and improvements of the various manual techniques, recognizing their shortcomings.

SUMMARY OF THE INVENTION

In the $CO_2$ analyzing apparatus and method of this invention deficiencies in prior techniques are overcome by utilization of a $CO_2$ separating or stripping procedure in which a relatively small and constant sidestream of liquid, such as wine, is tapped from the main line and is mixed with a carefully monitored stream of a carrier gas in which $CO_2$ is dissolved, preferably $N_2$, and ejected under the condition of a pressure differential into a $CO_2$ separating chamber. The pressure differential is sufficient to yield substantially instantaneous, substantially complete $CO_2$ evolution. The $CO_2$ is stripped by the $N_2$ carrier gas because of the greater solubility of $CO_2$ in the $N_2$ than in the depleted liquid, and the $CO_2$ is carried in the $N_2$ stream to a device for measuring and quantitatively indicating the $CO_2$ content. In the separating chamber remaining liquid is separated and drained from the evolved $CO_2$ and its $N_2$ carrier so that liquid is not introduced into the $CO_2$ measuring device. Ejection of the liquid with dissolved $CO_2$ into the separating chamber occurs in a high-speed intermittent fashion approaching a continuous ejection, with the pressure differential existing at each ejection for extremely rapid evolution of $CO_2$ into the $N_2$ gas phase.

In applicants' $CO_2$ analyzing apparatus and method the constant sidestream of wine with dissolved $CO_2$ tapped from the main wine line is conducted to a constant displacement metering pump means from which the wine is conducted to a check means which prevents flow of the wine until a desired build-up of pressure occurs in the line between the pumping means and the check device. A continuous flow of carefully monitored $N_2$ carrier gas is introduced into the check device for mixing of the $N_2$ with ejected wine passed through the checking device upon attainment of the desired pressure. The wine now mixed with $N_2$ is ejected into the separating chamber which is at a low pressure relative to that required to open the check device, and ejection results in extremely rapid evolution of $CO_2$ into the $N_2$ gas phase because of the shock-like effect of the pressure differential upon the ejected wine. From the separating chamber the combined $CO_2$ and $N_2$ gas is conducted to the $CO_2$ measuring device wth an associated recording means for permitting a continuous quantitative reading of $CO_2$ content, and the remaining liquid is separated, preferably by gravity, and permitted to drain from a drain device which at all times seals the interior of the separating chamber for preventing loss of $CO_2$ through the drain.

With the above described analyzing apparatus and method a continuous, quantitative reading of $CO_2$ content readily may be obtained. In essence, by the ejection technique of this invention, the unpredictability of $CO_2$ and the drawbacks of reliance upon measurements based on $CO_2$ partial pressure are avoided by measurement of the very rapidly evolved $CO_2$ under more effective control than achieved with prior techniques. Applicants' $CO_2$ analyzing technique now provides a procedure advantageously used during high-speed bottling operations, for example, where main line wine flow ranges on the order of 50–85 gal. per minute, as it yields an extremely accurate continuous indication of the amount of dissolved $CO_2$.

Accordingly, objects of this invention include provision of $CO_2$ analyzing apparatus and a method for accurate and continuous measurement and recording; analyzing apparatus and a method more advantageously employed in connection with high-speed beverage bottling operations than prior techniques; apparatus and a method which avoids resort to time-consuming manual procedures; and apparatus and a method in which dissolved $CO_2$ is evolved into a gas phase for measurement under conditions which are more favorable to accurate measurement than heretofore.

There are other objects and advantages of the invention as will become apparent from the following description of the preferred embodiment of the invention.

DESCRIPTION OF THE FIGURES

FIG. 1 is a schematic view illustrating the $CO_2$ analyzing apparatus and method of this invention; and FIG. 2 is a fragmentary view showing a preferred form of checking device utilized in this invention.

DESCRIPTION OF PREFERRED EMBODIMENT

Referring to FIG. 1, the invention generally comprises a constant displacement pumping means 10 which receives a beverage such as wine from a main line 11. The wine may be introduced to pumping means 10 through a line 12 which has imposed therein a valve 13 and a tap 14 through which the sidestream of wine may flow from line 11. From pumping means 10 the wine with dissolved $CO_2$ is conducted through the line 15 to a check device such as a check valve 16. Check valve 16 also receives a continuous flow of monitored carrier gas, such as $N_2$, from a gas source 17 through a line 18 in which is a valve 19. The $N_2$ stream is passed through a flow meter 22 then through line 23 into a portion of checking device 16.

A desirable form of checking device 16 (FIG. 2) comprises a seat 25 on which is sealingly seated an O-ring 26 which prevents passage of wine to be analyzed from line 15 when the check valve 16 is in the checking position. In such condition O-ring 26 is in sealing relationship with an interior valve member which includes a tapering, hollow, generally conical end portion 27 having a pair of apertures 28 in its conical surface. An integral hollow valve portion 29, the interior of which is in communication with the interior of valve portion 27, receives a helical spring 32 compressed between the inner surface of valve portion 29 and a spring seat 33 for normally urging valve portion 27 against and in sealing relationship with O-ring 26. Within check valve 16 and terminating in the interior of hollow valve portion 29 is an outlet 30 for the monitored $N_2$ from source 17. The interior of valve portion 29 communicates with stripping chamber 24 through a passage 34.

Chamber 24 (FIG. 1) is elongated and generally vertically disposed. At its upper end is a line 35 communicating between chamber 24 and a $CO_2$ measuring and recording device 36. At the lower or drain end of stripping chamber 24 is a drain line 37 having a junction with a secondary drain line 38. Lines 37 and 38 terminate in a sealing drain device 39 from which the spent wine is drained. One desirable conventional form of sealing drain device 39 is a diaphragm-type device, and when such device is employed, main drain line 37 communicates with a lower drain chamber 39a and secondary drain line 38 with an upper drain chamber 39b, such chambers being separated by a diaphragm 42.

In high-speed beverage bottling, as for example in wine bottling, a typical rate of flow for wine in main line 11 is on the order of 75 gal. per minute. For such an installation, it is desirable in a preferred embodiment of this invention to tap a sidestream 12 having a constant flow rate of approximately 400 cc. per hr. and pass such stream to a positive displacement metering pump which operates at approximately 90 strokes per minute. One suitable conventional pump is manufactured by Milton Roy Company under Model No. 19-60029-003 and is characterized by its delivery of a constant flow. The check valve 16 is typically adapted for opening when the pressure in line 15 reaches approximately 150 psi. $N_2$ gas from source 17 may preferably be introduced into line 18 at a pressure of approximately 15 psi. and flows through the flow meter 22 which permits a flow of 500 cc. per minute into the interior of valve portion 29 in check valve 16. The build-up of pressure in wine line 15 between metering pump 10 and check valve 16 serves an important function of preventing the wine from objectionably passing through the metering pump in an uncontrolled fashion. It serves a further important purpose of preventing premature evolution of the $CO_2$ from the wine until the occurance of the sudden ejection of the wine into separating chamber 24. Check valve 16 also rather importantly prevents back flow of dissolved $CO_2$ into the wine line which would affect accuracy of $CO_2$ measurement.

Separating chamber 24 is preferably a generally vertically elongated cylinder of approximately 1 inch in inside diameter and 15 inches long, although other dimensions may be employed. Combined $CO_2$ and $N_2$ flow through the upper portion of stripping chamber 24 and through line 35 to measuring and recording device 36 which provides a quantitative indication of $CO_2$ content. The rapid operation of metering pump 10, e.g. approximately 90 strokes per minute, and the resulting substantially constant delivery causes a high frequency of ejection into stripping chamber 24 which results in a $CO_2$ flow to measuring device 36 which approaches a desirable constant level.

The conventional measuring and recording device 36 may take the form of an infrared analyzer, such as a BECKMAN Model 315B. Such a device measures the differential in absorption of infrared energy in a two-beam system, one beam being passed through a flow-through sample cell containing the combined $CO_2$ and $N_2$ from separating chamber 24 and the other beam passing through a sealed reference cell containing a known $CO_2$—$_{N2}$ gas mixture, so that a quantitative measure may be obtained and recorded. For conservation of $N_2$ and reduction of the amount of wine which need be tapped from the main wine line 11, it is desired to utilize a reduced size sample cell in the infrared analyzer. Measuring and recording device 36 is of conventional construction and not separately illustrated. As the sample cell in the measuring device 36 is a flow-through cell the normal pressure within separating chamber 24 absent the introduction of wine under pressure from check valve 16 is substantially at or very slightly above atmospheric pressure. Thus when ejection occurs at the 150 psi. level at which check valve 16 opens a severe pressure differential exists resulting in the sudden evolution of $CO_2$ from the wine.

In stripping chamber 24 spent liquid wine is separated from the evolved $CO_2$ and drains through line 37 into the lower drain chamber 39a of a conventional sealing drain device, such as, for example, a diaphragm-type device manufactured by A. O. Smith under Model 29, Type 12. When such drain device is used a secondary line 38 communicates with an upper drain chamber 39b of the drain device 39. The drain device 39 permits flow through drain 43, but at a rate of flow that will result in continuous maintenance of an amount of spent wine in line 37. At all times line 37 above the level of the spent wine maintained therein is sealed from communication with outlet line 43.

For still wine, which is one beverage with which the above-described $CO_2$ analyzing apparatus and method are most advantageously employed, it can be expected that $CO_2$ content will be approximately in the 0.25 grams per 100 milliliter range. In testing of the apparatus of this invention on a wine line as above-described it was found that the accuracy of $CO_2$ measurement was high, approaching to within 5 milligrams per 100 milliliters or better. Test results show that approximately 98% of the dissolved $CO_2$ present in the sampled wine is stripped in chamber 24 by the carrier gas $N_2$. Federal Wine Regulations set forth allowable $CO_2$ levels in beverages such as still wine and refer to tolerances of approximately 9 milligrams of $CO_2$ per 100 milliliters, so that the accuracy of measurement with applicants' technique is well within such tolerances.

From the foregoing it can be seen that the analyzing apparatus and method of this invention involve generating a constant sidestream 12 of the liquid to be analyzed and generating a flow of monitored carrier gas from a source 17. In the presence of the carrier gas the liquid is ejected into the confined volume provided by stripping chamber 24 under conditions causing substantially instantaneous and substantially complete evolution of $CO_2$ from the liquid. The combined $CO_2$ and carrier gas is conducted to a $CO_2$ measuring and recording device 36 and the spent wine, depleted of $CO_2$, is drained from chamber 24.

It is to be understood that the claims appended hereto are intended to cover all changes and modifications of the example herein chosen for purposes of disclosure which do not depart from the spirit and scope of the invention. For example, while the invention has been described with reference to bottling of wines, it should be understood that the technique, with suitable modification, may be utilized in analysis of $CO_2$ level in any liquid containing dissolved $CO_2$.

We claim:

1. A method of determining the amount of carbon dioxide present in a continuously supplied liquid containing dissolved carbon dioxide comprising the steps of:
  a. generating a constant flow sidestream of said continuously supplied liquid;
  b. generating a continuous flow of a gas which dissolves carbon dioxide;
  c. in the presence of said gas ejecting said sidestream into a confined volume under the influence of a pressure differential sufficient to cause substantially instantaneous and substantially complete evolution of carbon dioxide from said liquid leaving said liquid substantially depleted of carbon dioxide;
  d. conducting the evolved carbon dioxide and said gas to a carbon dioxide measuring station and at said station measuring the amount of carbon dioxide in the combination of said gas with said carbon dioxide; and
  e. draining said liquid depleted of carbon dioxide from said confined volume.

2. The method of claim 1, wherein:
  f. said ejecting occurs at a frequency in excess of one ejection per second.

3. The method of claim 1, wherein:
  f. said gas is nitrogen.

4. The method of claim 1, wherein:
  f. said pressure in said confined volume is substantially atmospheric pressure.

5. The method of claim 1, wherein:
  f. in said confined volume said combined evolved carbon dioxide and gas are separated from said liquid depleted of carbon dioxide by gravity.

6. The method of claim 1, in which:
  f. said sidestream presented for said ejecting is wine at a rate of flow of approximately 400 cc. per hour; and
  g. said gas is nitrogen having a rate of flow of approximately 500 cc. per minute.

7. Apparatus for determining the amount of carbon dioxide present in a continuously supplied liquid containing dissolved carbon dioxide, comprising:
  a. means for generating a constant flow sidestream of said continuously supplied liquid;
  b. a continuous source of a gas which dissolves carbon dioxide;
  c. means defining a confined volume;
  d. means for ejecting said sidestream into said confined volume in the presence of said gas under the influence of a pressure differential sufficient to cause substantially instantaneous and substantially complete evolution of carbon dioxide from said liquid into said gas leaving said liquid substantially depleted of carbon dioxide;
  e. measuring means for measuring the amount of carbon dioxide in the combination of said gas with said carbon dioxide;
  f. a conduit between said confined volume and said measuring means; and
  g. drain means for draining said liquid depleted of said carbon dioxide from said confined volume.

8. The apparatus of claim 7, wherein:
  h. said ejecting means includes a check means for permitting a pressure build-up in said constant flow sidestream.

9. The apparatus of claim 8, including:
  i. a constant displacement pumping means in said sidestream for substantially constant delivery of said liquid to said ejecting means.

10. The apparatus of claim 7, wherein:
  h. said ejecting means is adapted for high-speed ejection of said sidestream into said confined volume at a frequency in excess of one ejection per second.

11. The apparatus of claim 7, wherein:
  h. said means defining said confined volume is an elongated generally vertically oriented chamber;
  i. said conduit communicates with the upper portion of said chamber; and
  j. said drain communicates with the lower portion of said chamber.

12. The apparatus of claim 7, wherein:
  h. said measuring means is an infrared analyzer device.

13. The apparatus of claim 7 wherein said source is a nitrogen source.

* * * * *